United States Patent [19]

Ackrell

[11] 4,064,141
[45] Dec. 20, 1977

[54] NOVEL ESTERS OF 6,11-DIHYDRODIBENZO-[B.E.]-THIEPIN-11-ONE-3-ALKANOIC ACIDS

[75] Inventor: Jack Ackrell, Palo Alto, Calif.

[73] Assignee: Syntex (U.S.A.) Inc., Palo Alto, Calif.

[21] Appl. No.: 706,866

[22] Filed: July 19, 1976

[51] Int. Cl.² .................. C07D 337/12; C07D 411/12
[52] U.S. Cl. ................................................. 260/327 B
[58] Field of Search ............ 260/327 B, 340.2, 340.9, 260/469

[56] References Cited

U.S. PATENT DOCUMENTS

| 2,979,514 | 4/1961 | O'Brien et al. | 260/340.2 |
|---|---|---|---|
| 3,852,333 | 12/1974 | Fisher | 260/471 R |
| 3,946,036 | 3/1976 | Gadient | 260/327 B |

Primary Examiner—Cecilia M. S. Jaisle
Attorney, Agent, or Firm—Gerard A. Blaufarb; William B. Walker

[57] ABSTRACT

Esters of 6,11-dihydrodibenzo-[b.e.]-thiepin-11-ones of the formula:

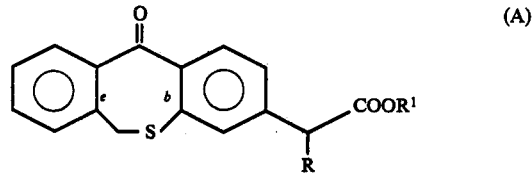

wherein R is hydrogen or methyl and $R^1$ is —CH$_2$—CH(OH)—CH$_2$OH,

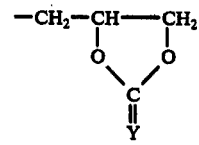

where Y is either O or S, or

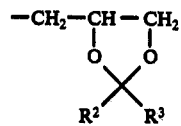

where $R^2$ and $R^3$ are independently hydrogen, alkyl having 1 to 6 carbon atoms, phenyl or benzyl or together $R^2$ and $R^3$ form an alkylene bridge having 4, 5 or 6 carbon atoms, and processes for the production thereof.

16 Claims, No Drawings

NOVEL ESTERS OF 6,11-DIHYDRODIBENZO-[b.e.]-THIEPIN-11-ONE-3-ALKANOIC ACIDS

This invention relates to novel esters of 6,11-dihydrodibenzo-[b.e.]-thiepin-11-ones represented by the following formula:

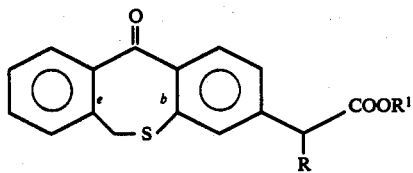

wherein R is hydrogen or methyl and $R^1$ is —CH$_2$—CH(OH)—CH$_2$OH,

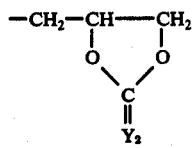

where Y is either O or S, or

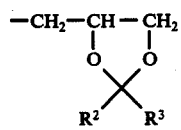

where $R^2$ and $R^3$ are independently hydrogen, alkyl having 1 to 6 carbon atoms, phenyl or benzyl, or together $R^2$ and $R^3$ form an alkylene bridge having 4, 5 or 6 carbon atoms.

As used in this specification and claims, the term "alkyl" refers to both straight and branched alkyl groups having from 1 to 6 carbon atoms, and thus includes primary, secondary and tertiary alkyl groups. Typical alkyl groups include for example, methyl, ethyl, n-propyl, isopropyl, n-butyl, isobutyl, t-butyl, n-amyl, n-hexyl and the like.

When R is H and $R^2$ and $R^3$ are the same the compounds of the present invention exist as (dl) mixtures. When R is H and $R^2$ and $R^3$ are different the compounds of the present invention exist as pairs of diastereomers, i.e., pairs of enanthiomorphs or (dl) mixtures.

When R is methyl the starting acid may be a (dl) mixture or the (d) enantiomorph.

When the (dl) acid is utilized as starting material and $R^2$ and $R^3$ are the same the compounds of this invention exist as pairs of diastereomers, i.e., pairs of enantiomorphs or (dl) mixtures. Similarly when the (d) acid is utilized as starting material and $R^2$ and $R^3$ are the same the compounds of the present invention exist as (dl) mixtures.

When the (dl) acid is utilized as starting material and $R^2$ and $R^3$ are different the compounds of this invention exist as 2 pairs of diastereomers or 4 pairs of enantiomorphs, whereas when the (d) acid is utilized as starting material and $R^2$ and $R^3$ are different the compounds of this invention exist as pairs of diastereomers, i.e., pairs of enantiomorphs or (dl) mixtures. The preferred compounds embraced by Formula (A) are those wherein $R^2$ and $R^3$ are the same and most preferably when $R^2$ and $R^3$ are both either hydrogen or methyl.

The novel compounds of the present invention can be prepared by a process illustrated by the following reaction sequence:

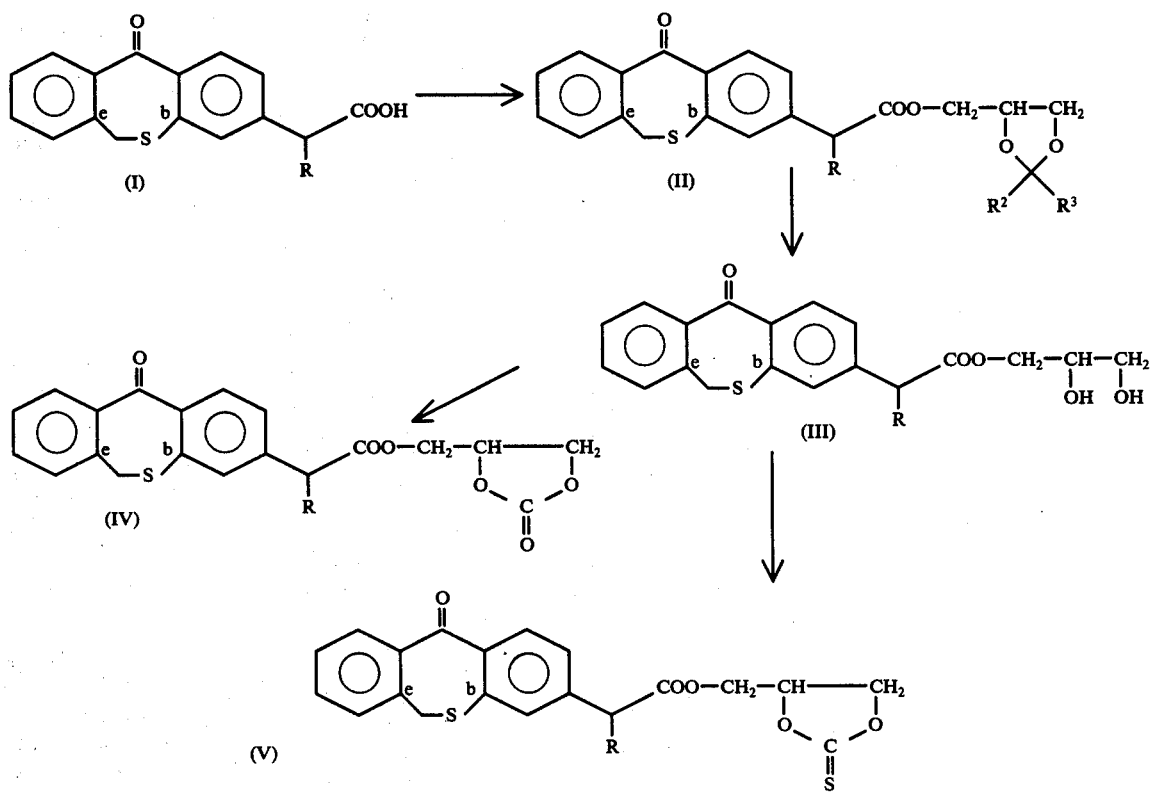

wherein R, $R^2$ and $R^3$ are as defined above.

In practicing the process depicted above, the starting materials of Formula (I), i.e., 6,11-dihydrodibenzo-[b.e.]-thiepin-11-one-3-acetic acid, (dl) 2-(6,11-dihydrodibenzo-[b.e.]-thiepin-11-one-3-yl)propionic acid and the (d) isomer of the latter, disclosed in my copending patent application Ser. No. 634,086 filed Nov. 11, 1975, are treated with p-toluenesulfonyl chloride and a dioxolane compound of the formula

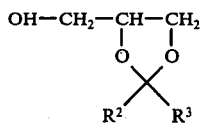

wherein $R^2$ and $R^3$ are as defined above, which reagent can be a racemic mixture when $R^2$ and $R^3$ are the same, or a mixture of diastereomers when $R^2$ and $R^3$ are different, in a tertiary amine as solvent, to produce the corresponding compound of Formula (II). This reaction is effected at a temperature of from about 0° to about 50° C, for a period of time of the order of 24 to about 90 hours. Examples of suitable tertiary amines used are pyridine, triethylamine, trimethylamine and the like. The reaction can be alternatively effected in the presence of an inert cosolvent, e.g., benzene, tetrahydrofuran, dimethoxyethane and the like.

In the preferred embodiments, the reaction is conducted in pyridine solution, at room temperature for about 48 hours.

Alternatively, the compounds of Formula (II) can be obtained by preparing initially the acid chloride via conventional methods, i.e., by treatment of the free acid (I) with thionyl chloride or oxalyl chloride, followed by treatment of the acid chloride with the dioxolane reagent in a suitable inert organic solvent, e.g., benzene, dimethoxyethane, tetrahydrofuran and the like, or mixtures thereof, in the presence of a tertiary amine, at about 0° to about 50° C, for about 24 to about 80 hours.

Upon acid treatment of the compounds of Formula (II) with a dilute mineral or organic acid, e.g., aqueous hydrochloric acid, aqueous sulfuric acid, aqueous acetic acid, aqueous chloroacetic acid and the like, in a solvent miscible with water such as acetone, methyl ethyl ketone, dioxane, tetrahydrofuran and the like, at a temperature of from about 0° to about 50° C, preferably at room temperature, for about 12 to about 24 hours, there is obtained the dihydroxyprop-1-yl ester of Formula (III).

By reaction of a compound (III) with phosgene in a suitable inert organic solvent or mixtures of solvents and in the presence of a tertiary amine, e.g., pyridine, there are obtained the corresponding oxo compounds of Formula (IV). The reaction usually takes place at room temperature (18° to 25° C), but, if desired, it can be carried out at relatively higher or lower temperatures, for about 12 to about 24 hours. Adequate solvents for this reaction are benzene, toluene, dioxane, dimethoxyethane, tetrahydrofuran and mixtures thereof.

Treatment of a dihydroxyester (IV) with thiocarbonyldiimidazole in a hydrocarbon solvent, at a temperature in the range from room temperature to the reflux temperature of the solvent used, for a period of time of the order of about 20 minutes to about 5 hours affords the corresponding 2-thioxo compound of Formula (V). Adequate solvents for this reaction are benzene, toluene, cyclohexane, xylene and the like. In the preferred embodiments the reaction is conducted in toluene solution, at reflux temperature for about 30 minutes.

Exemplary of the compounds prepared by the above described process, covered within the scope hereof are:

(2,2-dimethyl-1,3-dioxolan-4-yl)methyl 6,11-dihydrodibenzo-[b.e.]-thiepin-11-one-3-acetate,
(2,2-dimethyl-1,3-dioxolan-4-yl)methyl 2-(6,11-dihydrodibenzo-[b.e.]-thiepin-11-one-3-yl)propionate,
(2-methyl-1,3-dioxolan-4-yl)methyl 6,11-dihydrodibenzo-[b.e.]-thiepin-11-one-3-acetate,
(2-methyl-1,3-dioxolan-4-yl)methyl 2-(6,11-dihydrodibenzo-[b.e.]-thiepin-11-one-3-yl)propionate,
(2-hexyl-1,3-dioxolan-4-yl)methyl 6,11-dihydrodibenzo-[b.e.]-thiepin-11-one-3-acetate,
(2-hexyl-1,3-dioxolan-4-yl)methyl 2-(6,11-dihydrodibenzo-[b.e.]-thiepin-11-one-3yl)propionate,
(1,3-dioxolan-4-yl)methyl 6,11-dihydrodibenzo-[b.e.]-thiepin-11-one-3-acetate,
(1,3-dioxolan-4-yl)methyl 2-(6,11-dihydrodibenzo-[b.e.]-thiepin-11-one-3-yl)propionate,
(2-phenyl-1,3-dioxolan-4-yl)methyl 6,11-dihydrodibenzo-[b.e.]-thiepin-11-one-3-acetate,
(2-phenyl-1,3-dioxolan-4-yl)methyl 2-(6,11-dihydrodibenzo-[b.e.]-thiepin-11-one-3-yl)propionate,
(2-benzyl-1,3-dioxolan-4-yl)methyl 2-(6,11-dihydrodibenzo-[b.e.]-thiepin-11-one-3-yl)propionate,
[2,2-(1,4-tetramethylene)-1,3-dioxolan-4-yl]methyl 2-(6,11-dihydrodibenzo-[b.e.]-thiepin-11-one-3-yl)propionate,
[2,2-(1,5-pentamethylene)-1,3-dioxolan-4-yl]methyl 2-(6,11-dihydrodibenzo-[b.e.]-thiepin-11-one-3-yl)propionate,
[2,2-(1,6-hexamethylene)-1,3-dioxolan-4-yl]methyl 2-(6,11-dihydrodibenzo-[b.e.]-thiepin-11-one-3-yl)propionate,
2',3'-dihydroxy-prop-1'-yl 6,11-dihydrodibenzo-[b.e.]-thiepin-11-one-3-acetate,
2',3'-dihydroxy-prop-1'-yl 2-(6,11-dihydrodibenzo-[b.e.]-thiepin-11-one-3-yl)propionate,
(2-oxo-1,3-dioxolan-4-yl)methyl 6,11-dihydrodibenzo-[b.e.]-thiepin-11-one-3-acetate,
(2-oxo-1,3-dioxolan-4-yl)methyl 2-(6,11-dihydrodibenzo-[b.e.]-thiepin-11-one-3-yl)propionate,
(2-thioxo-1,3-dioxolan-4-yl)methyl 6,11-dihydrodibenzo-[b.e.]-thiepin-11-one-3-acetate, and
(2-thioxo-1,3-dioxolan-4-yl)methyl 2-(6,11-dihydrodibenzo-[b.e.]-thiepin-11-one-3-yl)propionate.

The compounds of Formula (A) are useful as anti-inflammatory agents, analgetic agents, platelet aggregation inhibitors, fibrinolytic agents, and as smooth muscle relaxants. They can be used both prophylactically and therapeutically.

The preferred compounds of Formula (A) are the esters wherein $R^2$ and $R^3$ are the same. Also preferred are the esters derived from (d) 2-(6,11-dihydrodibenzo-[b.e.]-thiepin-11-one-3-yl)propionic acid.

The compounds of Formula (A), exhibit anti-inflammatory, analgesic and anti-pyretic activities. Accordingly, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compound of Formula (A) in an appropriate pharmaceutical composition can be via any of the accepted modes of administration of agents for the treatment of inflammation, pain, or pyrexia, or the prophylaxis thereof. Thus, administration can be for example orally, parenterally, or topically, in the form of solid, semi-solid or liquid dosage forms, such as, for example, tablets, suppositories, pills, capsules, powders, liquids, suspensions, creams, lotions, ointments, or the like, preferably in unit dosage forms suitable for simple administration of precise dosages. The compositions will include a conventional pharmaceutical carrier or excipient and an active compound of Formula (A), and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 0.05 mg. to 10 mg. of the active compound of Formula (A), per kilogram of body weight is used. Most conditions respond to treatment comprising a dosage level of the order of 0.25 mg. to 3 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compound of Formula (A), may be formulated into a suppository using, for example, polyalkylene glycols, for example, polypropylene glycol, as the carrier. Liquid pharmaceutically administerable compositions can, for example, be prepared by dissolving, dispersing, etc., an active compound, as described above, and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emusifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pa., 14th Edition, 1970. The composition to be administered will, in any event, contain a quantity of the active compound(s) in a pharmaceutically effective amount for relief of the particular condition being treated in accordance with the teachings of this invention.

The compounds of Formula (A) described above, are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formula (A) are used as agents for delaying the onset of, or for postponing, parturition. As used in this application, the phrase "to delay the onset of parturition" is intended to cover that delay in parturition caused by the administration of the compounds of Formula (A), at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formula (A), after uterine muscle contractions have begun. The condition of the patient, including the time within the gestation period when the contractions have begun, the severity of the contractions and how long the contractions have taken place will affect the results achieved with the administration of the compounds of Formula (A). For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formula (A), for the purposes set forth herein, should be consistent with best and/or accepted medical (or veterinary) practices so as to maximize the benefits to the mother and the fetus. For example, administration should not be continued so long past full term that the fetus dies in utero.

In the practice of this aspect of the present invention, a therapeutically effective amount of a compound of Formula (A), or a pharmaceutical composition containing a compound of Formula (A), is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally or parenterally in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccarin, talcum, cellulose, glucose, sucrose, magnesium carbonate and the like. The active compound as defined above may be formulated as suppositories using, for example polyalkylene glycols, for example, polypropylene glycol, as the carrier. Liquid pharmaceutically administerable compositions can, for example, be prepared by dissolving, dispersing, etc., an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 14th Edition, 1970. The composition or formulation to be administered will, in any event, contain a quantity of the active compound(s) in an amount effective to delay the onset of parturition or to postpone parturition if uterine contractions have already begun. Generally a daily dose of from 5 mg. to about 250 mg. of the active compound per kilogram of body weight will be administered with administration being a single dose or up to three or four smaller doses regularly given throughout the day. The amount of active compound administered will, of course, depend on its relative activity.

The following Examples illustrate the invention but should not be considered as a limitation upon the scope thereof. Where necessary, examples are repeated to prepare additional material for subsequent examples.

EXAMPLE 1

A solution of 100 mg. of (dl) 4-hydroxymethyl 2,2-dimethyl-1,3-dioxolane, 150 mg. of (dl) 2-(6,11-dihydrodibenzo-[b.e.]-thiepin-11-one-3-yl)propionic acid and 1 ml. of pyridine is treated with a solution of 200 mg. of p-toluenesulfonyl chloride in 1 ml. of pyridine. The reaction mixture is stirred for 48 hours at room temperature and then poured into 100 ml. of water and extracted with ether (2 × 50 ml.). The combined extracts are dried over anhydrous sodium sulfate and evaporated, to yield a residue which is chromatographed on 10 g. of silica gel, eluting with hexane: ethyl acetate (7:1). Evaporation of the eluate under reduced pressure yields 175 mg. of (2,2-dimethyl-1,3-dioxolan-4-yl)methyl 2-(6,11-dihydrodibenzo-[b.e.]-thiepin-11-one-3-yl)propionate (II, R, $R^2$ and $R^3$ = Me), an oil, as a mixture of diastereomeric isomers, which has the following physical constants: U.V.: $\lambda_{max}^{MeOH}$ 248, 355 nm ($\epsilon$ 24800, 3010); I.R.: $\nu_{max}^{CHCl_3}$ 1730, 1640 cm$^{-1}$; N.M.R.:$\delta_{TMS}^{CDCl_3}$ 1.32 (s, 6H), 1.24 (d, 3H), 3.40–4.40 (m, 4H), 3.94 (s, 2H), 4.07 (s, 2H), 6.90–7.60 (m, 6H), 8.01 ppm. (d, 1H); M.S.: m/e 412 (M+).

Likewise, using (d) 2-(6,11-dihydrodibenzo-[b.e.]-thiepin-11-one-3-yl)propionic acid as starting material and (dl) 4-hydroxymethyl-2,2-dimethyl-1,3-dioxolane as reagent there is obtained the ester of (dl) 4-hydroxymethyl-2,2-dimethyl-1,3-dioxolane with (d) 2-(6,11-dihydrodibenzo-[b.e.]-thiepin-11-one-3-yl)propionic acid.

EXAMPLE 2

A mixture of 500 mg. of 6,11-dihydrodibenzo-[b.e.]-thiepin-11-one-3-acetic acid, 15 ml. of methylene chloride, 1 ml. of thionyl chloride and 1 drop of dimethylformamide is stirred at room temperature for 2 hours. The solution is evaporated to dryness, and the residue dissolved in 10 ml. of dry benzene, then reevaporated. A solution of 3 ml. of (dl) 4-hydroxymethyl-2,2-dimethyl-1,3-dioxolane and 1 ml. of pyridine in 15 ml. of tetrahydrofuran is added to the residue. After 72 hours the reaction mixture is poured into water and extracted with ether. The ethereal solution is washed, dried and evaporated to afford (2,2-dimethyl-1,3-dioxolan-4-yl)methyl 6,11-dihydrodibenzo-[b.e.]-thiepin-11-one-3-acetate (II, R = H, $R^2$ and $R^3$ = Me), a mixture of two enantiomorphs.

EXAMPLE 3

Example 1 is repeated using (dl) 4-hydroxymethyl-2-methyl-1,3-dioxolane, (dl) 4-hydroxymethyl-2-hexyl-1,3-dioxolane, (dl) 4-hydroxymethyl-1,3-dioxolane, (dl) 4-hydroxymethyl-2-phenyl-1,3-dioxolane, (dl) 4-hydroxymethyl-2-benzyl-1,3-dioxolane, 4-hydroxymethyl-2,2-(1,4-tetramethylene)-1,3-dioxolane, or 4-hydroxymethyl-2,2-(1,5-pentamethylene)-1,3-dioxolane or 4-hydroxymethyl-2,2-(1,6-hexamethylene)-1,3-dioxolane in place of (dl) 4-hydroxymethyl-2,2-dimethyl-1,3-dioxolane, to produce the corresponding esters of (dl) 2-(6,11-dihydrodibenzo-[b.e.]-thiepin-11-one-3-yl)propionic acid, namely:

(2-methyl-1,3-dioxolan-4-yl)methyl 2-(6,11-dihydrodibenzo-[b.e.]-thiepin-11-one-3-yl)propionate, (2-hexyl-1,3-dioxolan-4-yl)methyl 2-(6,11-dihydrodibenzo-[b.e.]-thiepin-11-one-3-yl)propionate, (1,3-dioxolan-4-yl)methyl 2-(6,11-dihydrodibenzo-[b.e.]-thiepin-11-one-3-yl)propionate, (2-phenyl-1,3-dioxolan-4-yl)methyl 2-(6,11-dihydrodibenzo-[b.e.]-thiepin-11-one-3-yl)propionate, (2-benzyl-1,3-dioxolan-4-yl)methyl 2-(6,11-dihydrodibenzo-[b.e.]-thiepin-11-one-3-yl)propionate,

[2,2-(1,4-tetramethylene)-1,3-dioxolan-4-yl]methyl 2-(6,11-dihydrodibenzo-[b.e.]-thiepin-11-one-3-yl)propionate,

[2,2-(1,5-pentamethylene)-1,3-dioxolan-4-yl]methyl 2-(6,11-dihydrodibenzo-[b.e.]-thiepin-11-one-3-yl)propionate and [2,2-(1,6-hexamethylene)-1,3-dioxolan-4-yl]methyl 2-(6,11-dihydrodibenzo-[b.e.]-thiepin-11-one-3-yl)propionate, as mixtures of diastereomeric isomers.

In a similar manner, there are obtained the corresponding dioxolanyl esters of (d) 2-(6,11-dihydrodibenzo-[b.e.]-thiepin-11-one-3-yl)propionic acid and the esters of 6,11-dihydrodibenzo-[b.e]-thiepin-11-one-3-acetic acid with the (dl) dioxolane reagents mentioned above.

EXAMPLE 4

A mixture of 250 mg. of (2,2-dimethyl-1,3-dioxolan-4-yl)methyl 2-(6,11-dihydrodibenzo-[b.e.]-thiepin-11-one-3-yl)propionate, 10 ml. of acetone and 3 ml. of 10% hydrochloric acid is stirred for 16 hours, at room temperature. The reaction mixture is then poured into water and extracted with ether. The extract is washed, dried and evaporated, to yield a gum which is chromatographed on 10 g. of silica gel, eluting with hexane:ethyl acetate (2:1). Evaporation of the eluate yields 2′,3′-dihydroxy-prop-1′-yl 2-(6,11-dihydrodibenzo-[b.e.]-thiepin-11-one-3-yl)propionate (III, R = Me), a mixture of diastereomeric isomers.

The same compound can be prepared using the dioxolanyl esters of (dl) 2-(6,11-dihydrodibenzo-[b.e.]-thiepin-11-one-3-yl)propionic acid listed in Example 3.

In a similar manner starting from the ester of (dl) 4-hydroxymethyl-2,2-dimethyl-1,3-dioxolane with (d) 2-(6,11-dihydrodibenzo-[b.e.]-thiepin-11-one-3-yl)propionic acid there is obtained 2′,3′-dihydroxy-prop-1′-yl) 2-(6,11-dihydrodibenzo-[b.e.]-thiepin-11-one-3-yl)propionate, as a racemic mixture.

Likewise, (2,2-dimethyl-1,3-dioxolan-4-yl) methyl 6,11-dihydrodibenzo-[b.e.]-thiepin-11-one-3-acetate is converted into 2′,3′-dihydroxy-prop-1′-yl 6,11-dihydrodibenzo-[b.e.]-thiepin-11-one-3-acetate.

EXAMPLE 5

A solution of 250 mg. of 2′,3′-dihydroxy-prop-1′-yl 2-(6,11-dihydrodibenzo-[b.e.]-thiepin-11-one-3-yl) propionate in 1.5 ml. of dry dioxane is added to 2 ml. of a 12% (w/v) solution of phosgene in benzene, containing 0.5 ml. of pyridine. The reaction mixture is kept at room temperature for 16 hours, and then poured into 100 ml. of water and 50 ml. of ethyl acetate. The organic layer is separated, dried over anhydrous sodium sulfate and evaporated to dryness, to yield (2-oxo-1,3-dioxolan-4-yl)methyl 2-(6,11-dihydrodibenzo-[b.e.]-thiepin-11-one-3-yl)propionate (IV, R = Me) as a mixture of diastereomers.

In a similar manner starting from 2′,3′-dihydroxiprop-1′-yl 2-(6,11-dihydrodibenzo-[b.e.]-thiepin-11-one-3-yl)propionate derived from (d) 2-(6,11-dihydrodibenzo-[b.e.]-thiepin-11-one-3-yl)propionate there is obtained (2-oxo-1,3-dioxolan-4-yl)methyl 2-(6,11-dihydrodibenzo-[b.e.]-thiepin-11-one-3-yl)propionate, as a racemic mixture.

Likewise 2′,3′-dihydroxy-prop-1′-yl 6,11-dihydrodibenzo-[b.e.]-thiepin-11-one-3-acetate is converted into (2-oxo-1,3-dioxolan-4-yl)methyl 6,11-dihydrodibenzo-[b.e.]-thiepin-11-one-3-acetate.

EXAMPLE 6

A mixture of 250 mg. of 2′,3′-dihydroxy-prop-1′-yl 2-(6,11-dihydrodibenzo-[b.e.]-thiepin-11-one-3-yl) propionate, 5 ml. of toluene and 200 mg. of thiocarbonyldiimidazole is refluxed for 30 minutes. The solution is cooled, poured into 25 ml. of water and extracted with ethyl acetate. The extract is dried over anhydrous sodium sulfate and evaporated, to yield a residue which is chromatographed on 10 g. of silica gel, eluting with hexane:ethyl acetate (6:1), thus obtaining (2-thioxo-1,3-dioxolan-4-yl)methyl 2-(6,11-dihydrodibenzo-[b.e.]-thiepin-11-one-3-yl)propionate (V, R = Me), a mixture of diastereomers.

In a similar manner, starting from 2′,3′-dihydroxy-prop-1′-yl 2-(6,11-dihydrodibenzo-[b.e.]-thiepin-11-one-3-yl)propionate derived from (d) 2-(6,11-dihydrodibenzo-[b.e.]-thiepin-11-one-3-yl)propionate there is obtained (2-thioxo-1,3-dioxolan-4-yl)methyl 2-(6,11-dihydrodibenzo-[b.e.] thiepin-11-one-3-yl)propionate, as a racemic mixture.

Likewise 2′,3′-dihydroxy-prop-1′-yl 6,11-dihydrodibenzo-[b.e.]-thiepin-11-one-3-acetate is converted into (2-thioxo-1,3-dioxolan-4-yl)methyl 6,11-dihydrodibenzo-[b.e.]-thiepin-11-one-3-acetate.

What is claimed is:

1. A compound selected from the group of those represented by the formula:

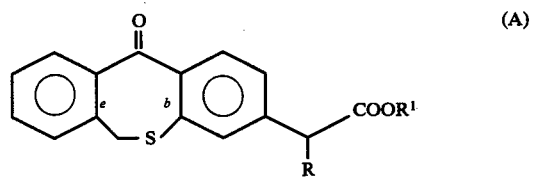

(A)

wherein R is hydrogen or methyl and $R^1$ is —$CH_2$—CH(OH)—$CH_2OH$,

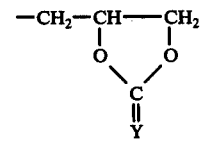

where Y is either O or S, or

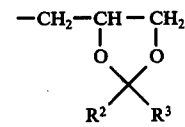

where $R^2$ and $R^3$ are independently hydrogen, alkyl having 1 to 6 carbon atoms, phenyl or benzyl, or together $R^2$ and $R^3$ form an alkylene bridge having 4, 5 or 6 carbon atoms.

2. A compound of claim 1 wherein $R^1$ is —$CH_2$—CH(OH)—$CH_2OH$.

3. A compound of claim 1 wherein $R^1$ is

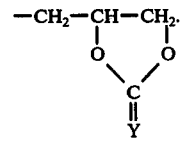

4. A compound of claim 3 wherein Y is O.
5. A compound of claim 3 wherein Y is S.
6. A compound of claim 1 wherein $R^1$ is

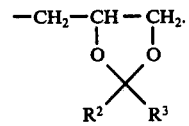

7. A compound of claim 6 wherein $R^2$ and $R^3$ are both methyl.

8. The compound of claim 2 wherein R is hydrogen, 2',3'-dihydroxy-prop-1'-yl 6,11-dihydrodibenzo-[b.e.]-thiepin-11-one-3-acetate.

9. A compound of claim 2 wherein R is methyl, 2',3'-dihydroxy-prop-1'-yl 2-(6,11-dihydrodibenzo-[b.e.]-thiepin-11-one-3-yl)propionate.

10. The compound of claim 4 wherein R is hydrogen, (2-oxo-1,3-dioxolan-4-yl)methyl 6,11-dihydrodibenzo-[b.e.]-thiepin-11-one-3-acetate.

11. A compound of claim 4 wherein R is methyl, (2-oxo-1,3-dioxolan-4-yl)methyl 2-(6,11-dihydrodibenzo-[b.e.]-thiepin-11-one-3-yl)propionate.

12. The compound of claim 5 wherein R is hydrogen, (2-thioxo-1,3-dioxolan-4-yl)methyl 6,11-dihydrodibenzo-[b.e.]-thiepin-11-one-3-acetate.

13. A compound of claim 5 wherein R is methyl, (2-thioxo-1,3-dioxolan-4-yl)-methyl 2-(6,11-dihydrodibenzo-[b.e.]-thiepin-11-one-3-yl)propionate.

14. The compound of claim 7 wherein R is hydrogen, (2,2-dimethyl-1,3-dioxolan-4-yl)methyl 6,11-dihydrodibenzo-[b.e.]-thiepin-11-one-3-acetate.

15. A compound of claim 7 wherein R is methyl, (2,2-dimethyl-1,3-dioxolan-4-yl)methyl 2-(6,11-dihydrodibenzo-[b.e.]-thiepin-11-one-3-yl)propionate.

16. The compound of claim 15 wherein said compound is the ester of (dl) 4-hydroxymethyl-2,2-dimethyl-1,3-dioxolane with (d) 2-(6,11-dihydrodibenzo-[b.e.]-thiepin-11-one-3-yl)propionic acid.

* * * * *